(12) United States Patent
Margaria (10) Patent No.: US 11,154,678 B2
(45) Date of Patent: Oct. 26, 2021

(54) CUSTOMIZED SEALING MEMBER USING STOCK MATERIAL

(71) Applicant: KONINKLIJKE PHILIPS N.V., Eindhoven (NL)

(72) Inventor: Elizabeth Powell Margaria, Pittsburgh, PA (US)

(73) Assignee: Koninklijke Philips N.V., Eindhoven (NL)

(*) Notice: Subject to any disclaimer, the term of this patent is extended or adjusted under 35 U.S.C. 154(b) by 501 days.

(21) Appl. No.: 16/061,714

(22) PCT Filed: Dec. 9, 2016

(86) PCT No.: PCT/IB2016/057470
§ 371 (c)(1),
(2) Date: Jun. 13, 2018

(87) PCT Pub. No.: WO2017/109628
PCT Pub. Date: Jun. 29, 2017

(65) Prior Publication Data
US 2018/0369528 A1 Dec. 27, 2018

Related U.S. Application Data

(60) Provisional application No. 62/270,828, filed on Dec. 22, 2015.

(51) Int. Cl.
*A61M 16/06* (2006.01)
*A61B 5/00* (2006.01)
(Continued)

(52) U.S. Cl.
CPC ....... *A61M 16/0605* (2014.02); *A61B 5/0064* (2013.01); *A61B 5/1077* (2013.01);
(Continued)

(58) Field of Classification Search
CPC ...... A61M 2016/0661; A61M 2207/00; A61M 2207/02
See application file for complete search history.

(56) References Cited

U.S. PATENT DOCUMENTS 10,596,340 B2 * 3/2020 Kirchberger ...... A61M 16/0688
2007/0215161 A1 9/2007 Frater et al.
(Continued)

FOREIGN PATENT DOCUMENTS

FR 2988003 A1 * 9/2013 ........ A61M 16/0622
WO 2011049548 A1 4/2011
WO 2013144797 A1 10/2013

*Primary Examiner* — LaToya M Louis
(74) *Attorney, Agent, or Firm* — Michael W. Haas (57) ABSTRACT

A customized sealing member is for a customized mask. The customized mask includes a support member. The customized sealing member is manufactured by the process of generating surface geometry data of a face of a patient, the surface geometry data corresponding to and representing a surface geometry of the face of the patient; providing a directing apparatus shaped according to the surface geometry data, the directing apparatus being structured to receive and direct a stock of material; and inserting the stock of material into the directing apparatus in order to produce the customized sealing member.

17 Claims, 10 Drawing Sheets

(51) Int. Cl.
  *A61B 5/107*    (2006.01)
  *G06F 19/00*    (2018.01)
  *B33Y 80/00*    (2015.01)

(52) U.S. Cl.
  CPC .............. *A61M 16/06* (2013.01); *G06F 19/00* (2013.01); *A61M 2016/0661* (2013.01); *A61M 2207/00* (2013.01); *B33Y 80/00* (2014.12)

(56) References Cited

U.S. PATENT DOCUMENTS

| | | |
|---|---|---|
| 2012/0234326 A1 | 9/2012 | Mazzone et al. |
| 2014/0332007 A1 | 11/2014 | Znamenskiy et al. |
| 2015/0238719 A1 | 8/2015 | Chodkowski, Jr. |
| 2015/0273170 A1 | 10/2015 | Bachelder et al. |

* cited by examiner

CUSTOMIZED SEALING MEMBER USING STOCK MATERIAL

CROSS-REFERENCE TO PRIOR APPLICATIONS

This application claims the priority benefit under 35 U.S.C. § 371 of International Patent Application No. PCT/IB2016/057470, filed on Dec. 9, 2016, which claims the priority benefit of U.S. Provisional Patent Application No. 62/270,828, filed on Dec. 22, 2015, the contents of which are herein incorporated by reference.

BACKGROUND OF THE INVENTION

1. Field of the Invention

The present invention relates to non-invasive ventilation and pressure support systems wherein a patient interface device is used to deliver a flow of breathing gas to a patient, and in particular to customized sealing members and customized masks for patient interface devices. The present invention also relates to methods of manufacturing customized sealing members.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping. Non-invasive ventilation and pressure support therapies as just described involve a gas flow generator to produce a flow of breathing gas, and the placement of a patient interface device including a mask component on the face of a patient. The gas flow generator produces positive air pressure by taking air in from the surroundings and spinning a fan to push the air out of the machine, through a delivery conduit, and into the patient interface device to be delivered to the patient.

Traditional masks include a sealing feature and a support feature that is connected to the sealing feature. The support feature compresses the face to create a robust seal and to mechanically couple the mask to the face to prevent the mask from moving throughout the night. The support feature, unlike the sealing feature, imparts relatively large compressive forces onto the face of the patient. The sealing feature is typically very thin and has minimal intrinsic strength. A known problem with many traditional masks is that they are uncomfortable and provide a poor seal, as a result of the fact that a single mask geometry will be made for many different patients.

Customized masks address many deficiencies of known masks by improving comfort and seal. However, existing technologies to manufacture customized masks are expensive and inefficient. For example, generating a new mold for each new component requires new tooling to be made for each customized component, and is therefore undesirably expensive and inefficient.

SUMMARY OF THE INVENTION

Accordingly, it is an object of the present invention to provide a customized sealing member and a customized mask including the customized sealing member. The steps to manufacture the customized sealing member include generating surface geometry data of a face of a patient, the surface geometry data corresponding to and representing a surface geometry of the face of the patient; providing a directing apparatus shaped according to the surface geometry data, the directing apparatus being structured to receive and direct a stock of material; and inserting the stock of material into the directing apparatus in order to produce the customized sealing member.

The customized mask includes the customized sealing member and a support member coupled to the customized sealing member.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a," "an," and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs.

As employed herein, the statement that two or more parts or components "engage" one another shall mean that the parts exert a force against one another either directly or through one or more intermediate parts or components. As employed herein, the term "number" shall mean one or an integer greater than one (i.e., a plurality). As used herein, the term "geometry" shall mean a three-dimensional profile of a surface or object.

As employed herein, the term "three-dimensional scanner" shall mean a device that analyzes a real-world object and generates data (e.g., digital data) that represents the shape of the object in three dimensions, and shall include, without limitation, contact scanners that probe the subject through physical touch to generate the shape data, non-contact active scanners that emit some kind of radiation or light and detect its reflection or passing through the object to generate the shape data, and non-contact passive scanners that detect reflected ambient radiation to generate the shape data. As employed herein, the term "rendering" shall mean an image generated from two-dimensional or three-dimensional data that represents the shape of the object.

Figure 1:
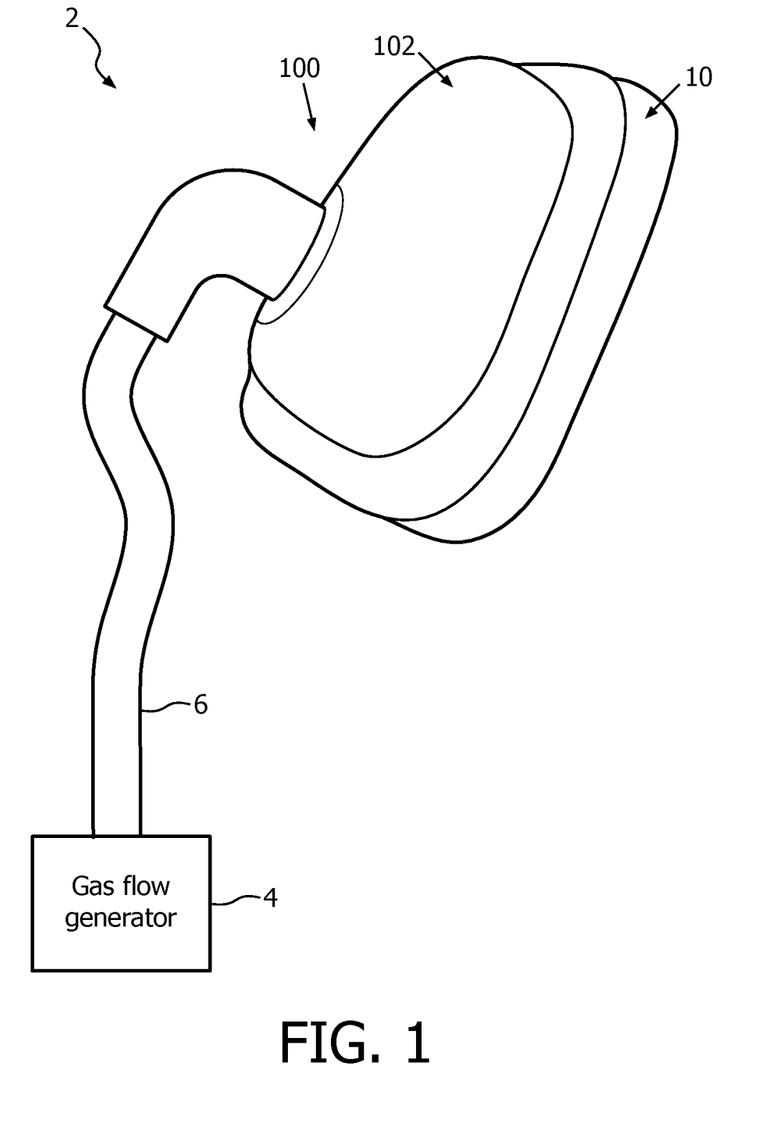
FIG. 1 is simplified view of a pressure support system including a customized mask, in accordance with a non-limiting embodiment of the disclosed concept.

FIG. 1 shows a pressure support system 2 in accordance with a non-limiting exemplary embodiment of the disclosed concept. The example pressure support system 2 includes a gas flow generator 4 (shown in simplified form), a gas delivery conduit (e.g., without limitation, hose 6, shown in simplified form), and a customized mask 100. Customized mask 100 is structured to engage and provide a seal with the face of a patient. Hose 6 fluidly couples gas flow generator 4 to customized mask 100 in order to allow pressure support therapy to be delivered to an airway of the patient. Customized mask 100 includes a support member (e.g., without limitation, faceplate 102) and an annular-shaped (with respect to a peripheral portion engaging faceplate 102) customized sealing member 110 coupled to faceplate 102. In the exemplary embodiment, faceplate 102 and customized sealing member 110 are separate components (i.e., are not made from the same piece of material) that are coupled to each other during manufacturing of customized mask 100, as will be discussed below. As will also be discussed in greater detail below, customized sealing member 110 provides a comfortable and reliable seal with the face of the patient, and is made by a relatively efficient and inexpensive novel manufacturing process.

Figure 2:
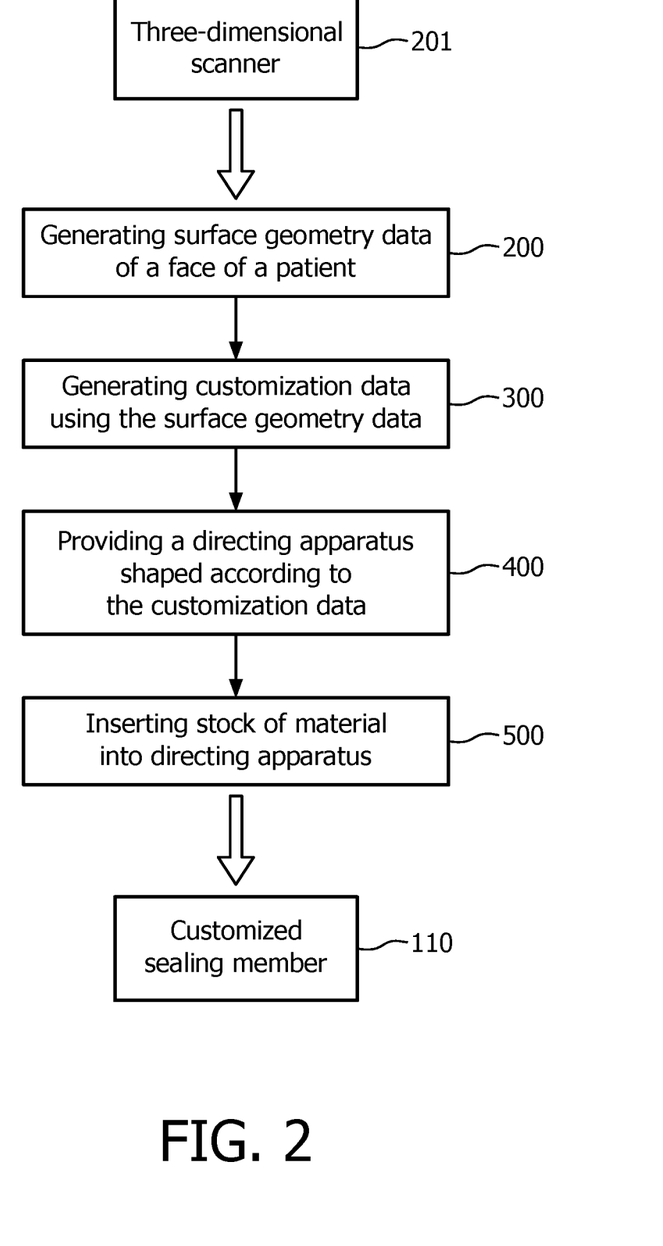
FIG. 2 is a schematic flow diagram, in block form, of a manufacturing process for a customized sealing member of the customized mask of FIG. 1.

More specifically, FIG. 2 shows a schematic flow diagram, in block form, of a process to manufacture customized sealing member 110, according to one non-limiting exemplary embodiment of the disclosed concept. The first step 200 is generating surface geometry data that corresponds to and represents a surface geometry of the face of a patient. In one exemplary embodiment, the generating step 200 includes scanning the face of the patient with a three-dimensional scanner 201 to generate the surface geometry data. It will be appreciated that other suitable alternative methods of generating surface geometry data may also be employed without departing from the scope of the disclosed concept. An example rendering 202 corresponding to the surface geometry data generated in step 200 as shown on, for example, a computer screen, is shown in FIG. 3.

Figure 3:
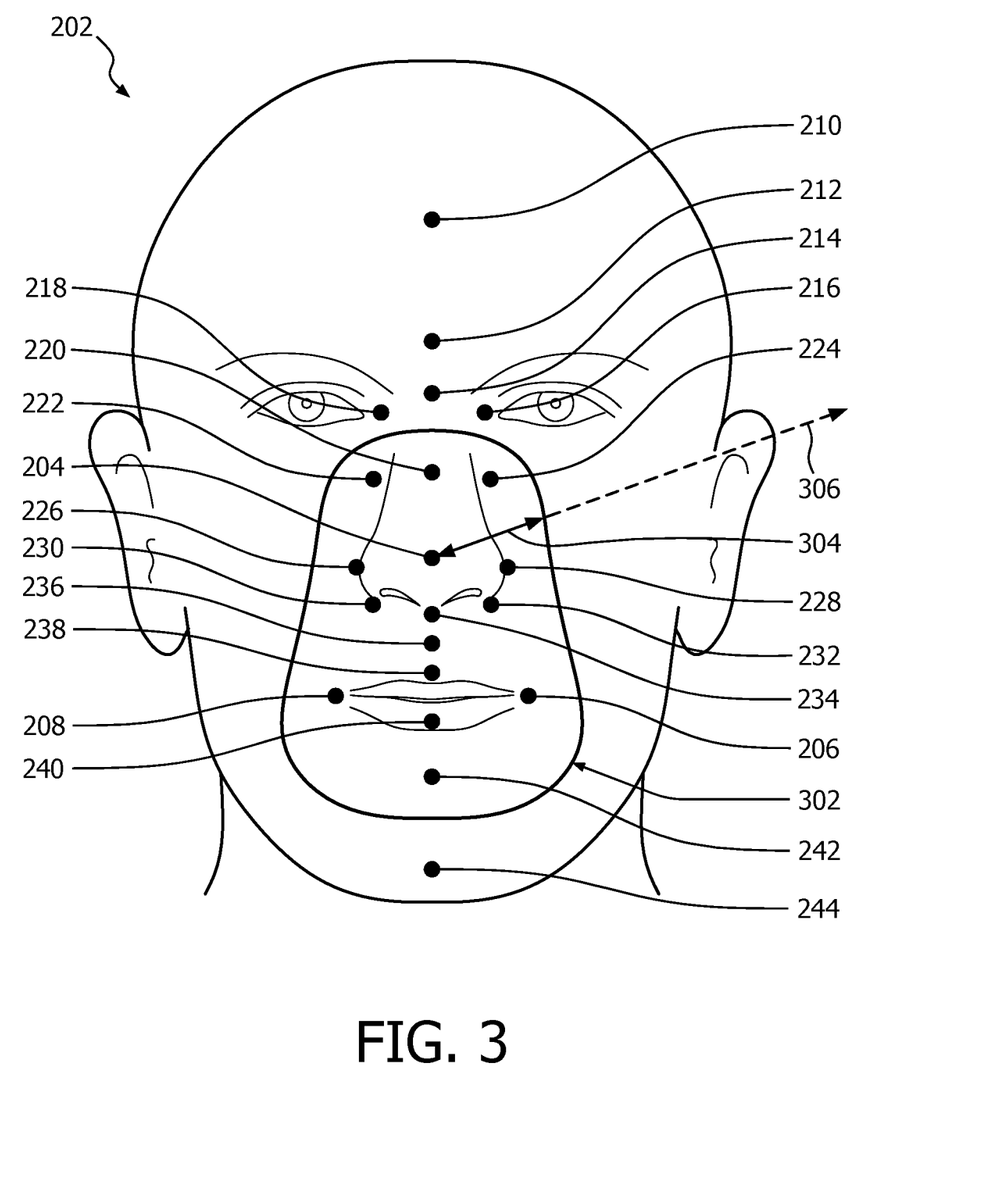
FIG. 3 is a top plan view of a rendering corresponding to surface geometry data of a face of a patient.

Continuing to refer to FIG. 3, in the exemplary embodiment, the surface geometry data has data representing a number of localized regions of the face of the patient (e.g., without limitation, nose tip region 204 and mouth corner regions 206, 208, central forehead region 210, bottom forehead region 212, nose bridge region 214, inner eye regions 216, 218, central nose bone region 220, central nose-cheek interface regions 222, 224, distal nose wing regions 226, 228, distal nose base regions 230, 232, central nose bottom region 234, central nasal landing region 236, central upper lip region 238, central lower lip region 240, central chin deep region 242, and chin apex region 244).

Referring again to FIG. 2, the process of the current exemplary embodiment further includes a second step 300 of employing an algorithm to generate customization data using the surface geometry data. The customization data of the present, non-limiting exemplary embodiment is represented in FIG. 3 in the form of a two-dimensional curvilinear indicia 302 located in a plane generally parallel to the face of the patient. Curvilinear indicia 302 is, in the present embodiment, represented by a set of two-dimensional coordinates that are unique to the particular patient face being scanned and that are determined from the surface geometry data. For example, as shown, one location of curvilinear indicia 302 is spaced a predetermined distance 304 in a predetermined direction 306 from nose tip region 204. It will be appreciated that the algorithm may use any number of localized regions 204, 206, 208, 210, 212, 214, 216, 218, 220, 222, 224, 226, 228, 230, 232, 234, 236, 238, 240, 242, 244 to generate the data representing each location of curvilinear indicia 302.

Figure 4:
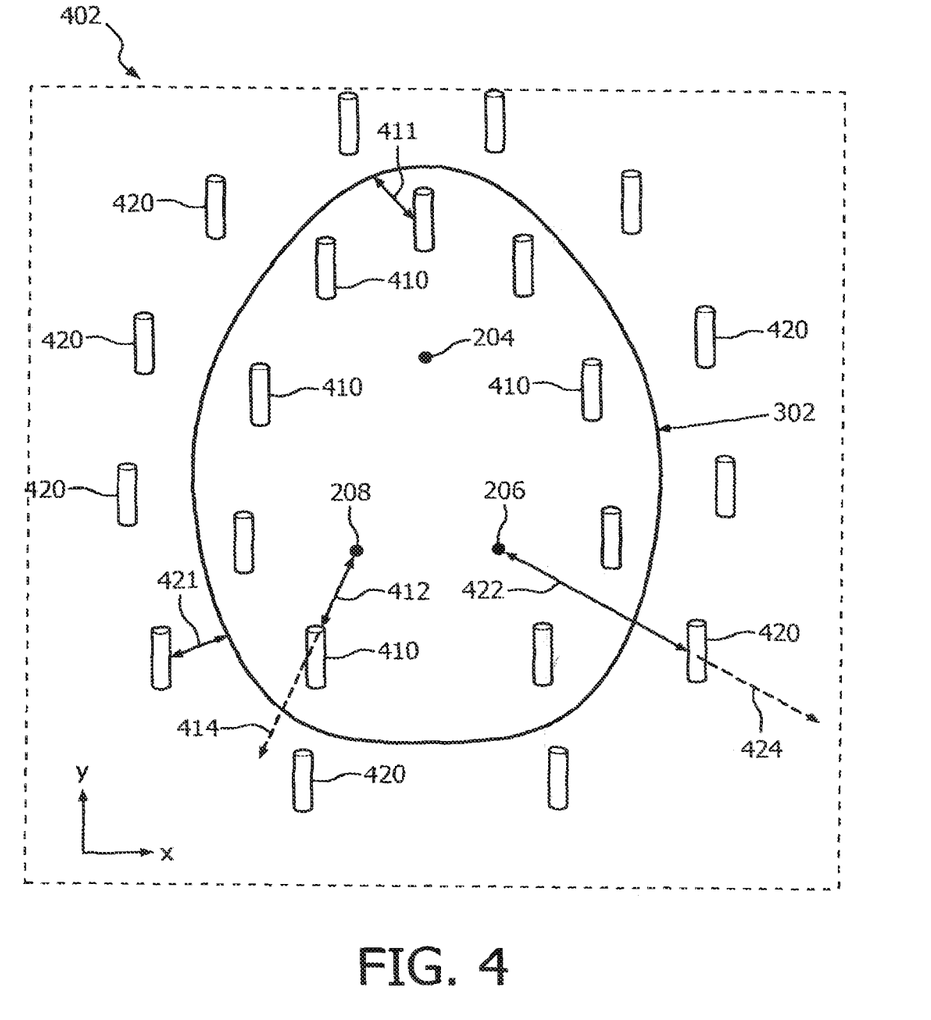
FIG. 4 is a simplified view of a directing apparatus employed in the manufacturing process of FIG. 2

The manufacturing process further includes the step 400 of providing a directing apparatus 402 (FIG. 4) shaped according to the customization data generated in step 300. As shown in FIG. 4, directing apparatus 402 includes an inner directing portion that includes a plurality of selectively movable inner rollers 410 and an outer directing portion that includes a plurality of selectively movable outer rollers 420. Rollers 410 are located internal with respect to rollers 420. That is, a closed curve extending through a center point of each of rollers 410 is located entirely within a closed curve that extends through each of rollers 420. Curvilinear indicia 302 is shown superimposed in FIG. 4 between first and second plurality of rollers 410, 420. In this non-limiting, exemplary embodiment, the bottom of each of the rollers 410, 420 is located in the same plane, and each roller is selectively movable in two dimensions (x and y dimensions as shown in FIG. 4). For example, each of the rollers 410, 420 may be manually movable/positionable using any suitable configuration such as a pegboard configuration. As another example, each of the rollers 410, 420 may be automatically movable to selected coordinate positions by a suitable drive means and computer control.

In the illustrated embodiment of FIG. 4, the inner directing portion defined by the closed curve of inner rollers 410 is positioned a predetermined distance 411 internal from curvilinear indicia 302, and the outer directing portion defined by the closed curve of outer rollers 420 is positioned a predetermined distance 421 external from curvilinear indicia 302. In one particular, non-limiting embodiment, predetermined distance 411 is the same as predetermined distance 421, advantageously allowing curvilinear indicia 302 to be centrally located in directing apparatus 402. Furthermore, the inner directing portion defined by the closed curve of inner rollers 410 has a circumferential length (i.e., a length of the closed curve extending through a center point of each respective roller 410) that is less than a circumferential length of curvilinear indicia 302, and the outer directing portion defined by the closed curve of outer rollers 420 has a circumferential length (i.e., a length of the closed curve extending through a center point of each respective roller 420) that is greater than the circumferential length of curvilinear indicia 302.

Figure 5:
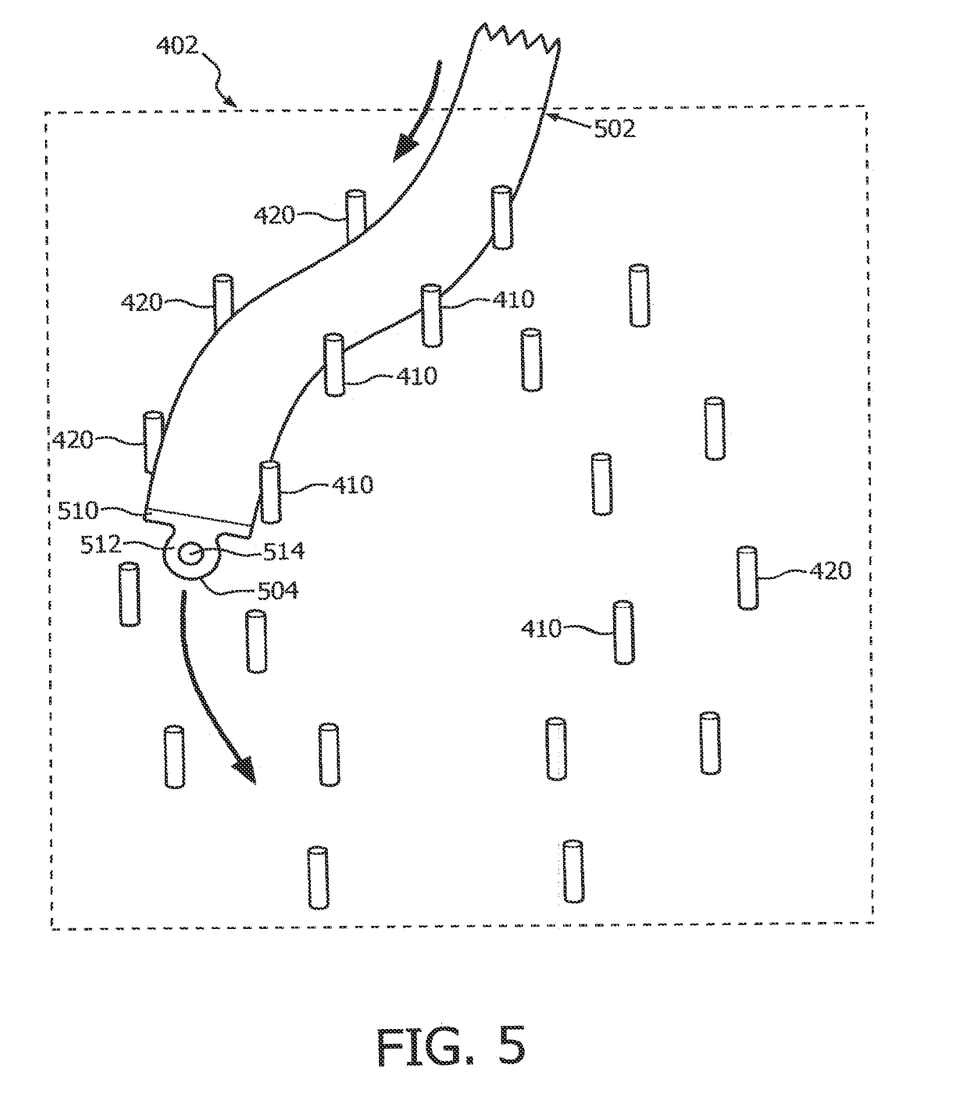
FIG. 5 is a simplified view of the directing apparatus of FIG. 4, and shown with a stock of material partially inserted.

Directing apparatus 402 as just described is structured to receive and direct a stock of material 502 (FIGS. 5-7) in order to form stock of material 502 in a customized manner. In the exemplary embodiment, rollers 410, 420 are each structured to rotate about a longitudinal axis, although it will be appreciated that in an alternative embodiment, similar suitable alternative rollers (not shown) may be employed to rotate in an alternative manner, or to remain generally fixed and operate solely as deflection members rather than as rollers. Accordingly, the manufacturing process further includes the step 500 of inserting stock of material 502 (FIGS. 5-7) into directing apparatus 402 between the inner directing portion defined by the closed curve of inner rollers 410 and the outer directing portion defined by the closed curve of outer rollers 420 in order to produce customized sealing member 110. As shown in FIG. 5, stock of material 502 has an end portion 504. It will be appreciated with reference to FIGS. 5-7 that when stock of material 502 is inserted into directing apparatus 402, end portion 504 is moved around the inner directing portion defined by the closed curve of inner rollers 410. That is, rollers 410, 420 advantageously cause stock of material 502 to bend around the inner directing portion defined by the closed curve of inner rollers 410 such that in the final position depicted in FIG. 7, the inner directing portion defined by the closed curve of inner rollers 410 is located entirely internal (i.e., each respective roller 410 engages an inner edge portion of stock of material 502) with respect to stock of material 502.

In other words, as stock of material 502 is inserted into directing apparatus 402, the outer directing portion defined by the closed curve of outer rollers 420 cooperatively engages and exerts a normal force on stock of material 502 radially inwardly to prevent stock of material from moving outwardly with respect to the outer directing portion defined by the closed curve of outer rollers 420 while the inner directing portion defined by the closed curve of inner rollers 410 cooperatively simultaneously engages and exerts an opposing normal force on stock of material 502 radially outwardly to prevent stock of material 502 from moving radially inwardly with respect to the inner directing portion defined by the closed curve of inner rollers 410. In this manner, stock of material 502 becomes shaped according to the surface geometry data. The disclosed method and manufacturing process may be employed for any number of different patients.

When stock of material 502 is inserted between the inner directing portion defined by the closed curve of inner rollers 410 and the outer directing portion defined by the closed curve of outer rollers 420, and is bent (i.e., shaped or formed) by rollers 410, 420 to form the finished profile of customized sealing member 110, stock of material 502 maintains a uniform cross-sectional profile. In this manner, customized sealing member 110 is structured to be made of a material that is suitable for bending and forming such as, for example and without limitation, a foam or a polymer such as an elastomer (e.g., silicone or rubber). By contrast, traditional prior art sealing flap structures and materials are not suitable for withstanding such bending without buckling into undesired shapes that would result in an inferior seal with the face of a patient.

Figure 6:
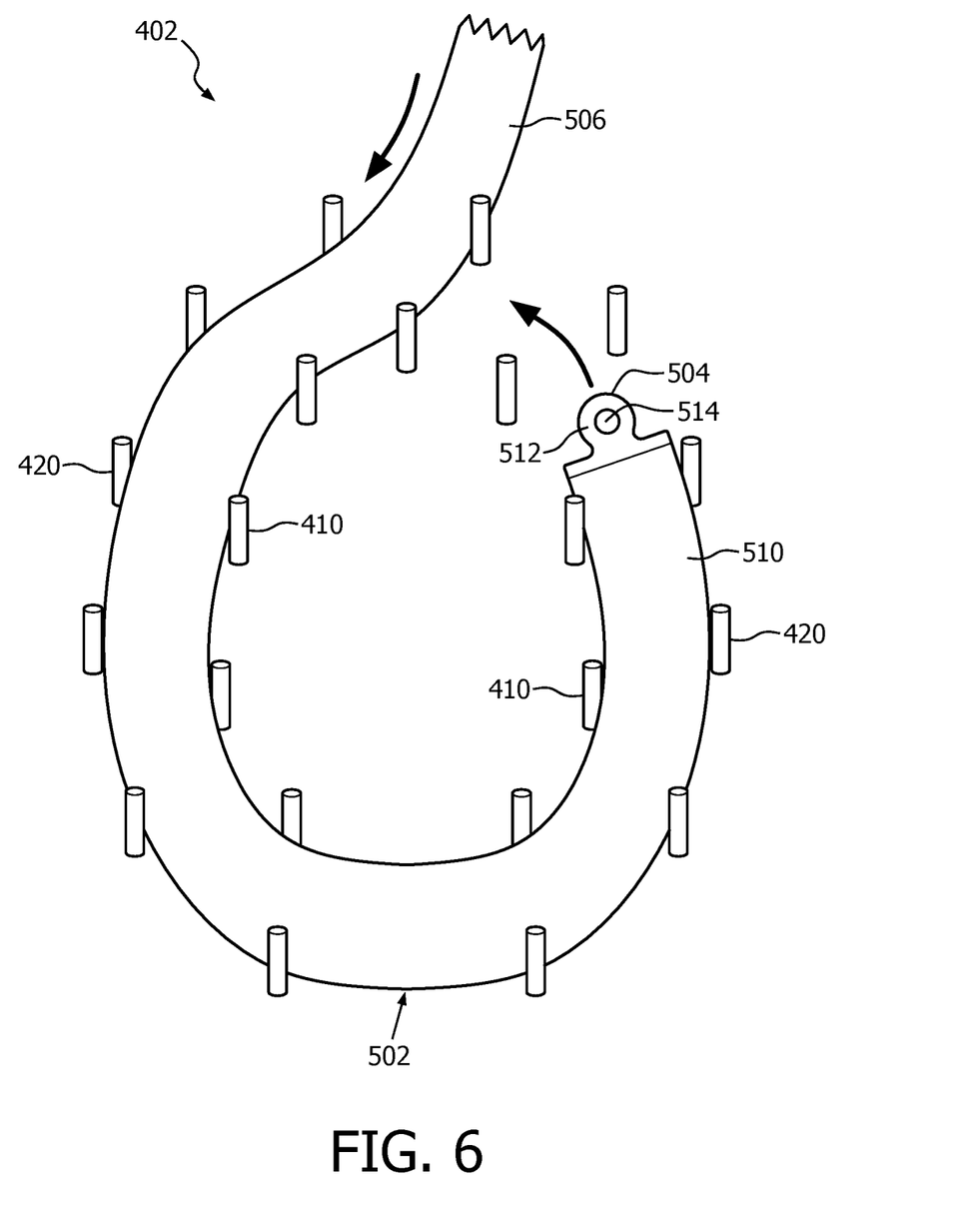
FIG. 6 is a simplified view of the directing apparatus of FIG. 5, and shown with the stock of material further inserted.
Figure 7:
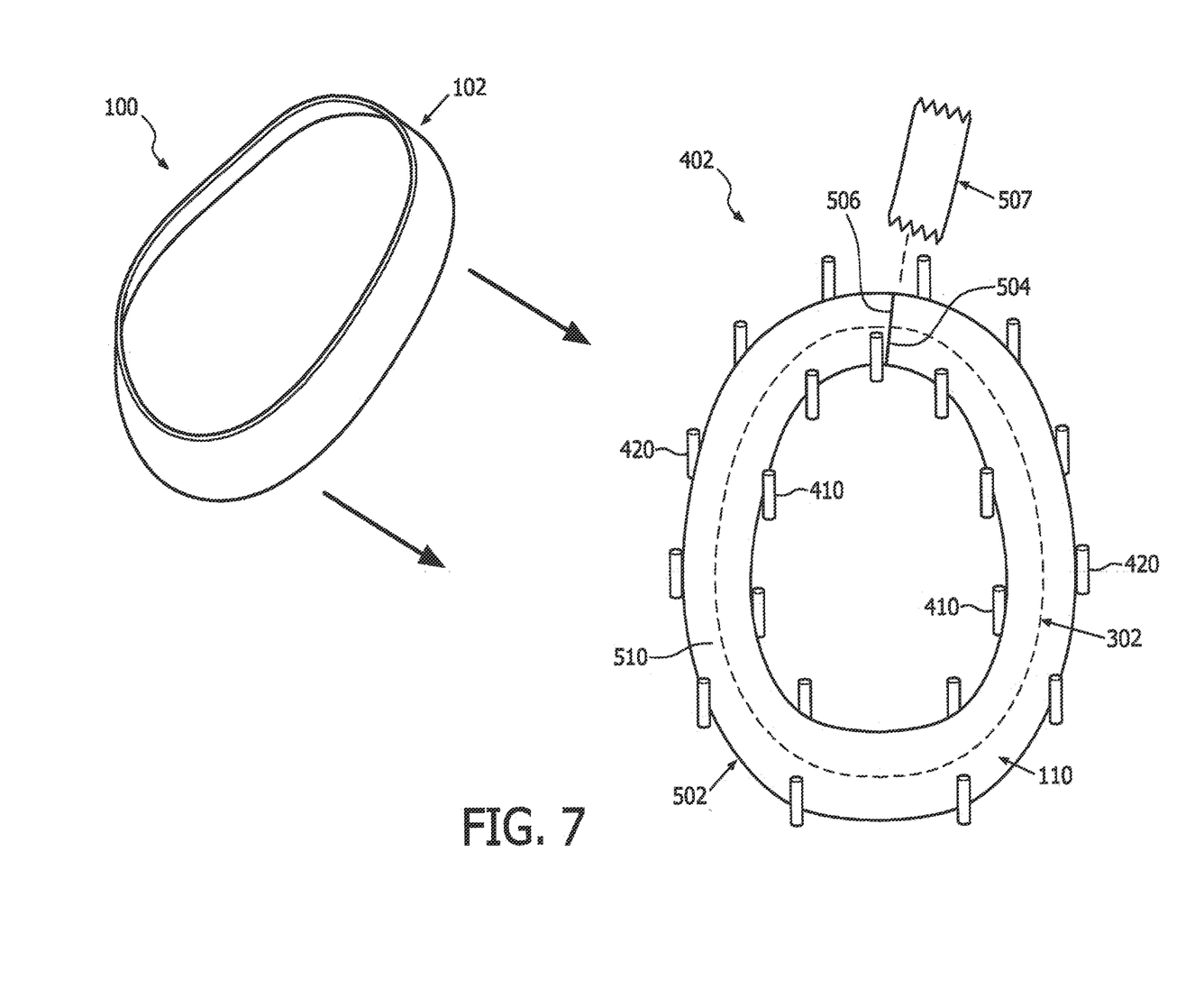
FIG. 7 is a simplified view of the directing apparatus of FIG. 6, showing a customized sealing member fully formed by the stock of material, and with a support member exploded.

Referring to FIGS. 6 and 7, stock of material 502 further includes a coupling portion 506 located opposite end portion 504. When stock of material 502 moves around the inner directing portion defined by the closed curve of inner rollers 410, coupling portion 506 moves toward the inner directing portion defined by the closed curve of inner rollers 410 until coupling portion 506 and end portion 504 approach each other. In this manner, the manufacturing process further includes the step of coupling end portion 504 to coupling portion 506 after end portion 504 moves around the inner directing portion defined by the closed curve of inner rollers 410. As shown in FIG. 7, end portion 504 and coupling portion 506 have been coupled to each other in order to form customized sealing member 110. In the exemplary embodiment, an excess portion 507 of stock of material 502 is shown remaining after stock of material 502 has been cut and coupling portion 506 has been coupled to end portion 504.

Referring again to FIGS. 5 and 6, stock of material 502 includes an elongated planar portion 510 and an elongated cylindrical-shaped portion 512 extending from planar portion 510. Cylindrical-shaped portion 512 has a thru hole 514 extending longitudinally therethrough, and is structured to engage and provide a seal with the face of the patient. By having thru hole 514, customized sealing member 110 is advantageously able to compress against the face of the patient and deflect, thereby providing a relatively comfortable seal with the face of the patient. Furthermore, it will be appreciated with reference to FIG. 7 that planar portion 510 is coupled to faceplate 102 in order to form customized mask 100. Customized sealing member 110 is coupled to faceplate 102 by any suitable mechanism known in the art (e.g., without limitation, being adhesively bonded).

Figure 8:
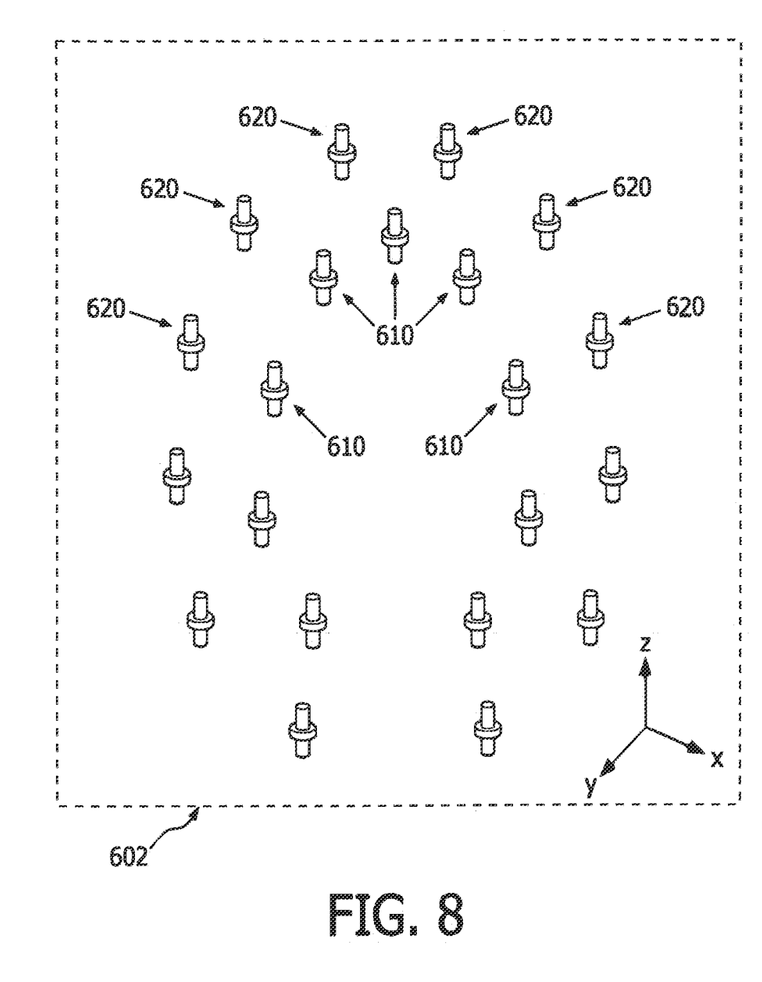
FIG. 8 is a simplified view of another directing apparatus, in accordance with an alternative embodiment of the disclosed concept.
Figure 9A:
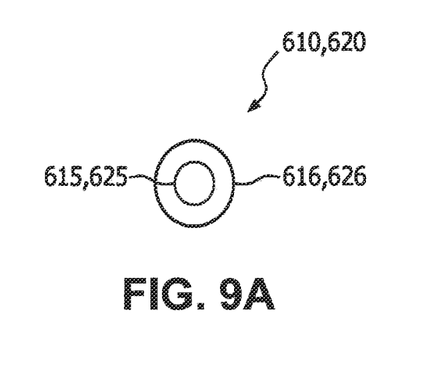
FIGS. 9A, 9B, and 9C are, respectively, a top plan view of a roller of the directing apparatus of FIG. 8, a front view of an inner roller of the directing apparatus of FIG. 8, and a front view of an outer roller of the directing apparatus of FIG. 8.
Figure 9B:
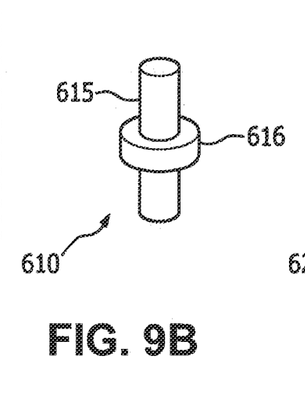
Figure 9C:
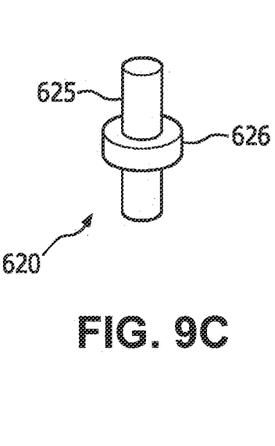

In the exemplary embodiment just described in connection with FIGS. 2-6, the customization data (curvilinear indicia 302) and the movement/adjustment of directing apparatus 402 is in two-dimensions only. It will be understood, however, that such an embodiment is merely exemplary, and that the customization data and the movement/adjustment of a directing apparatus similar to directing apparatus 402 may also be in three dimensions within the scope of the disclosed concept. For example, FIG. 8 shows a simplified view of an alternative directing apparatus 602 that may be employed to manufacture customized sealing member 110 instead of directing apparatus 402, in accordance with another non-limiting, exemplary embodiment wherein three-dimensional data and three-dimensional movement/adjustment is employed.

Also in this embodiment, directing apparatus 602 includes a number of selectively movable inner rollers 610 and a number of selectively movable outer rollers 620. As shown in FIGS. 8 and 9A-C, each respective roller 610, 620 includes a body portion 615, 625 and a shelf portion 616, 626 extending outwardly from the respective body portion 615, 625. As shown in the top plan view of FIG. 9A, in the exemplary embodiment, shelf portions 616, 626 are circularshaped, although other shapes are contemplated. In this embodiment, each of the rollers 610, 620 is movable in three dimensions (x, y, and z as shown in FIG. 8) such that the location of each of the rollers 610, 620 is adjustable in the x and y directions and such that the locations of the shelf portions 616, 626 in the z direction is adjustable. In the exemplary embodiment, these adjustments are made based on the three-dimensional customization data that is generated as described. For example, each of the rollers 610, 620 may be manually movable/positionable using any configuration suitable so secure each respective roller 610, 620 in three dimensions where the z dimension may be different for each respective roller 610, 620, or may be automatically movable to selective coordinate positions by a suitable drive means and computer control. It will be appreciated that by employing shelf portions 616, 626, the shape of customized sealing member 110 is advantageously able to be further controlled. More specifically, a depth of customized sealing member 110 in the z-direction is able to be further controlled by positioning rollers 610, 620 predetermined distances in predetermined directions in the z-direction based on the surface geometry data and allowing shelf portions 616, 626 to provide surfaces for stock of material 502 to rest on.

In the embodiments described with respect to FIGS. 2-8 and 9A-C, the position of the rollers 410, 420, 610, 620 was based on particular customization data that was generated from the obtained surface geometry data. Such an implementation, however, is not meant to be limiting. Rather, in further alternative embodiments, the position (i.e., coordinates) of rollers 410, 420 and 610, 620 may instead be determined directly from the attained surface geometry data as opposed to being determined from the intermediate customization data. For example, in another non-limiting, exemplary embodiment, each respective roller 410, 420 has a set of two-dimensional coordinates that are determined directly from the surface geometry data. In such an implementation, rollers 410, 420 may be positioned directly based on one or more of the localized regions 204, 206, 208, 210, 212, 214, 216, 218, 220, 222, 224, 226, 228, 230, 232, 234, 236, 238, 240, 242, 244 (FIG. 3). In order to determine the two-dimensional coordinates of each respective roller 410, 420, in this alternative embodiment, the providing step 400 includes employing a predetermined algorithm with the data representing localized regions 204, 206, 208, 210, 212, 214, 216, 218, 220, 222, 224, 226, 228, 230, 232, 234, 236, 238, 240, 242, 244 to generate data representing the sets of two-dimensional coordinates of rollers 410, 420. For example, as shown in FIG. 4, one of the rollers 410 is spaced a predetermined distance 412 in a predetermined direction 414 from localized region 208. Similarly, one of the rollers 420 is spaced a predetermined distance 422 in a predetermined direction 424 from localized region 206. It will be appreciated that the sets of two-dimensional coordinates of each of rollers 410, 420 are similarly spaced predetermined distances in predetermined directions from localized regions 204, 206, 208 according to the predetermined algorithm. Once rollers 410, 420 are positioned as described, manufacturing proceeds as described elsewhere herein.

As another example, in another non-limiting, alternative embodiment, each respective roller 610, 620 (FIGS. 8 and 9A-C) has a set of three-dimensional coordinates that are determined directly from the surface geometry data as opposed to being determined from the intermediate customization data. In such an implementation, rollers 610, 620 may be positioned directly based on one or more of the localized regions 204, 206, 208, 210, 212, 214, 216, 218, 220, 222, 224, 226, 228, 230, 232, 234, 236, 238, 240, 242, 244 (FIG. 3). In order to determine the three-dimensional coordinates of each respective roller 610, 620, in this alternative embodiment, the providing step 400 includes employing a predetermined algorithm with the data representing localized regions 204, 206, 208, 210, 212, 214, 216, 218, 220, 222, 224, 226, 228, 230, 232, 234, 236, 238, 240, 242, 244 to generate data representing the sets of three-dimensional coordinates of rollers 610, 620. Once rollers 610, 620 are positioned as described, manufacturing proceeds as described elsewhere herein.

Figure 10:
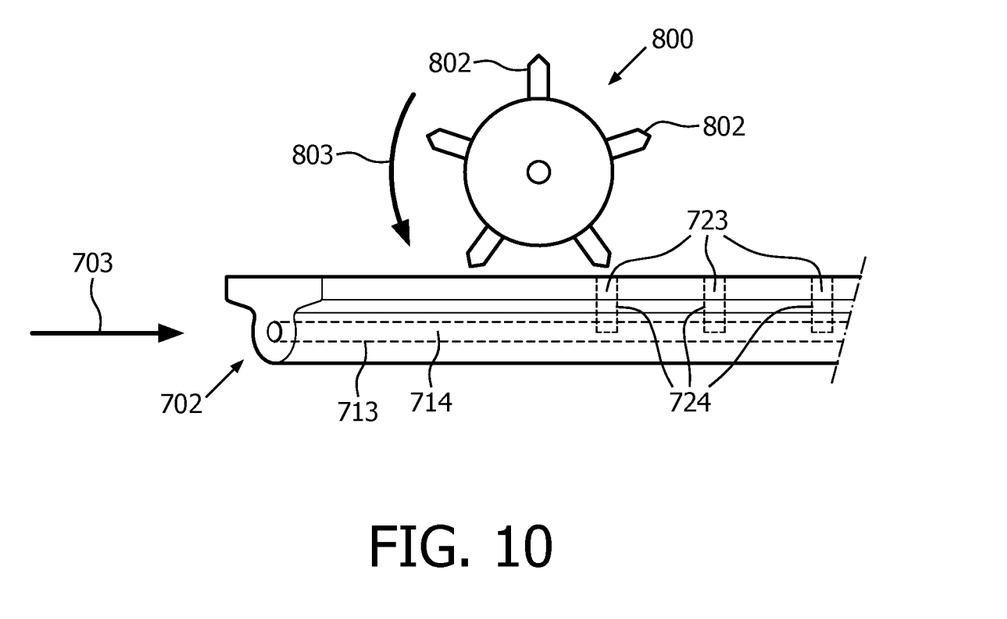
FIG. 10 shows a perforating apparatus, employed with a portion of a stock of material.
Figure 11:
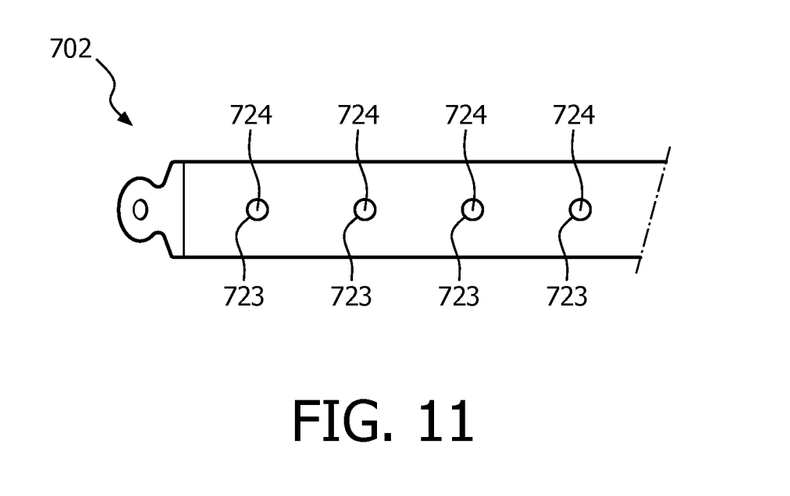
FIG. 11 shows a top plan view of the portion of the stock of material of FIG. 10.

FIG. 10 shows a portion of another stock of material 702 and a perforating apparatus 800, in accordance with another non-limiting embodiment of the disclosed concept. As shown, perforating apparatus 800, which includes a number of elongated perforating members 802, is structured to rotate in a direction 803 while stock of material 702 moves in a direction 703 past perforating apparatus 800. As stock of material 702 is moving past perforating apparatus 800, perforating members 802 extend into and create perforations 724 in stock of material 702 (see, for example, a number of edge portions 723 which each define a respective perforation 724). Additionally, stock of material 702, like stock of material 502, includes an edge portion 713 that defines a thru hole 714 extending longitudinally through stock of material 702. In the example shown and described herein, edge portions 723 intersect and are generally perpendicular with edge portion 713. In this manner, thru hole 714 is in fluid communication with each of the perforations 724. FIG. 11 shows a top plan view of a portion of stock of material 702, showing perforations 724.

Figure 12:
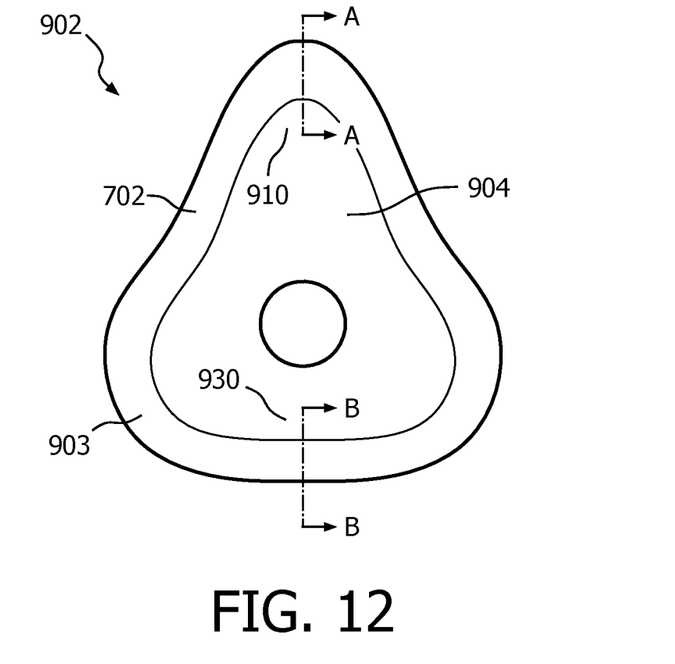
FIG. 12 shows a top plan view of a customized mask, in accordance with another non-limiting embodiment of the disclosed concept.
Figure 13:
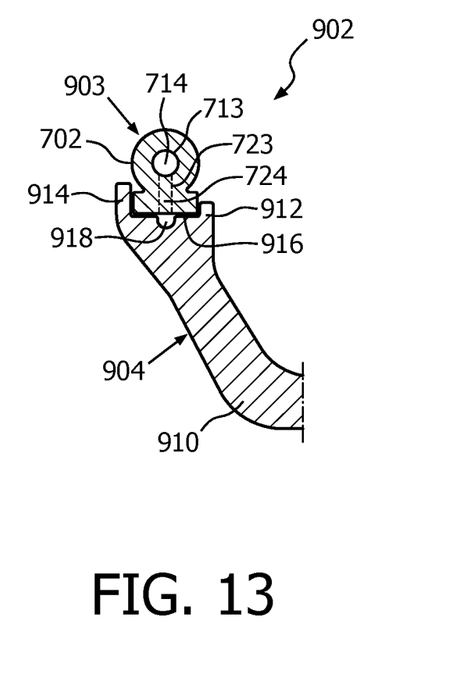
FIG. 13 shows a section view of the customized mask of FIG. 12, taken along line A-A of FIG. 12.

FIG. 12 shows a top plan view of a customized mask 902, which includes stock of material 702 in the form of a customized sealing member 903, and a support member (e.g., without limitation, faceplate 904) coupled to customized sealing member 903. It will be appreciated that customized sealing member 903 is formed by stock of material 702 in any manner substantially the same as those described hereinabove in association with customized sealing member 110, after being perforated by perforating apparatus 800. In the instant example described herein, faceplate 904 includes a nose bridge region 910 and a chin region 930 located opposite nose bridge region 910. As seen in FIG. 13, nose bridge region 910 includes a pair of opposing retaining portions 912,914 and a shelf portion 916 extending between retaining portions 912,914. Retaining portions 912,914 and shelf portion 916 each engage and retain customized sealing member 903. Additionally, shelf portion 916 has a recessed channel portion 918 extending from proximate customized sealing member 903 away from customized sealing member 903, and being structured to be located directly below edge portion 723.

Figure 14:
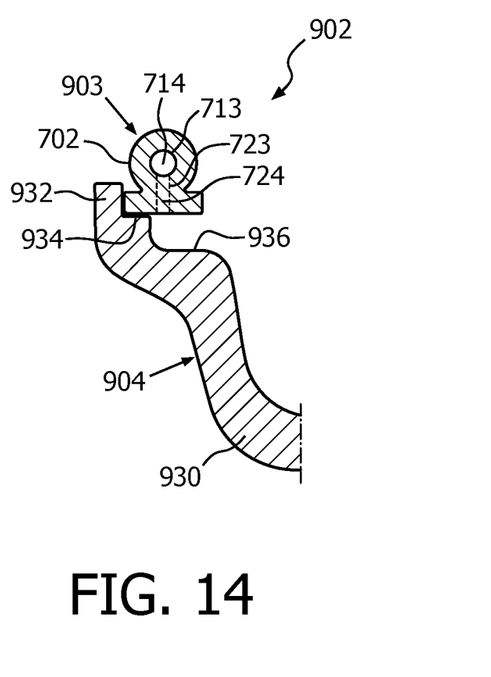
FIG. 14 shows another section view of the customized mask of FIG. 12, taken along line B-B of FIG. 12.

As seen in FIG. 14, chin region 930 includes a retaining portion 932 and a shelf portion 934 extending inwardly from retaining portion 932 toward an interior of faceplate 904. Together, retaining portion 932 and shelf portion 934 engage and retain customized sealing member 903. Additionally, chin region 930 further includes another shelf portion 936 spaced from and parallel to shelf portion 934, and being located directly below edge portion 723. In this manner, chin region 930 has a relatively large opening to allow access from an interior of faceplate 904 to perforation 724. As a result, when customized mask 902 is donned by a patient, breathing gas from a gas flow generator (e.g., without limitation, gas flow generator 4, shown in FIG. 1) is able to be communicated into perforations 724 proximate chin region 930 by way of the access opening, or fluid pathway between shelf portions 934,936. Referring again to FIG. 13, recessed channel portion 918 extends along the entire perimeter of faceplate 904 except near chin region 930. Accordingly, recessed channel portion 918 operates as a feeder to direct breathing gas to each of the perforations 724 along the entire perimeter and into the thru hole 714, after it has passed through the access opening, or fluid pathway, between shelf portions 934,936. By allowing the breathing gas to enter thru hole 714, the breathing gas is advantageously able to inflate customized sealing member 903, thereby providing a more robust and comfortable seal with the face of the patient.

The disclosed novel manufacturing process advantageously allows sealing members, such as sealing members 110,903 to be customized in a manner that is relatively inexpensive and efficient. More specifically, equipment is not wasted in that rollers 410, 420, 610, 620 are structured to be repeatedly used to manufacture numerous customized sealing members for any different patient. All that is required is a facial scan by three-dimensional scanner 201, employing a predetermined algorithm with the facial scan to determine where to position rollers 410, 420, 610, 620, inserting a stock of material between rollers 410, 420, 610, 620 and coupling a coupling portion to an end portion of the stock of material. Referring to FIG. 7, it will be appreciated that customized sealing member 110 has a length that is the same as the length of curvilinear indicia 302, shown superimposed in FIG. 7 in dashed line drawing. In this manner, sealing members 110,903 are customized and are thus able to provide a comfortable and reliable seal with the face of the patient.

Additionally, although the disclosed concept has been described herein in association with directing apparatus 402, 602 being in the form of spaced apart inner rollers 410, 610 and outer rollers 420, 620 it will be appreciated that a similar suitable alternative directing apparatus (not shown) may be employed in order to perform the desired function of directing stock of materials 502, 702 to produce customized sealing members 110,903. For example and without limitation, it is within the scope of the disclosed concept to employ additional rollers located between, but above and/or below, inner rollers 410 and outer rollers 420 to further control shape in a third dimension (i.e., in the z-direction into and out of the face of the patient). It is also within the scope of the disclosed concept to not include rollers, but rather include a continuous track mechanism to direct stock of materials 502, 702, or, though not as economically efficient, to employ a fixed mold (e.g., a mold printed with a three-dimensional printer based on the surface geometry data) in order to direct stock of materials 502, 702. It will also be appreciated that although customized sealing members 110, 903 are structured to be employed in full-face customized masks 100,902, similar suitable alternative sealing members (not shown) such as, for example and without limitation, customized cradle-style sealing members, customized nasal sealing members, and/or customized pillows-style sealing members, may be employed in similar suitable alternative customized masks, without departing from the scope of the disclosed concept.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A customized sealing member for a customized mask, the customized mask comprising a support member, the customized sealing member being manufactured by the process of:
    generating surface geometry data of a face of a patient, the surface geometry data corresponding to and representing a surface geometry of the face of the patient;
    providing a directing apparatus shaped according to the surface geometry data, the directing apparatus comprising an inner directing portion defining a first closed curve shaped according to the surface geometry data, and an outer directing portion defining a second closed curve shaped according to the surface geometry data, the directing apparatus being structured to receive and direct a stock of material, the stock of material comprising an end portion and a coupling portion disposed opposite the end portion, wherein the inner directing portion comprises a first plurality of rollers each having a set of first coordinates, and wherein the outer directing portion comprises a second plurality of rollers each having a set of second coordinates;
    inserting the stock of material into the directing apparatus in order to produce the customized sealing member;
    inserting the stock of material between the inner directing portion and the outer directing portion; and
    moving the end portion around the first closed curve defined by the inner directing portion such that as the end portion moves around the inner directing portion, the coupling portion moves toward the inner directing portion until the coupling portion and the end portion meet when the end portion has moved around the first closed curve defined by the inner directing portion.

2. The customized sealing member according to claim 1, wherein the process further comprises the step of:
    generating customization data based on the surface geometry data, the directing apparatus being shaped based on the customization data.

3. The customized sealing member according to claim 1, wherein the surface geometry data has first data representing a localized region of the surface geometry; wherein the process further includes the step of:
    generating customization data using the surface geometry data, the customization data representing a curvilinear indicia, the curvilinear indicia being spaced a predetermined distance
in a predetermined direction from the localized region.

4. The customized sealing member according to claim 3, wherein the providing step further comprises:
    positioning the inner directing portion a predetermined distance internal from the curvilinear indicia; and positioning the outer directing portion a predetermined distance external from the curvilinear indicia.

5. The customized sealing member according to claim 3, wherein the curvilinear indicia has a first circumferential length; and wherein the customized sealing member has a second circumferential length the same as the first circumferential length.

6. The customized sealing member according to claim 1, wherein the surface geometry data has first data representing a localized region of the surface geometry; and wherein the process further comprises the steps of:
   employing the first data to generate customization data representing a curvilinear indicia; and
   employing the customization data to generate second data representing each respective set of first coordinates and third data representing each respective set of second coordinates.

7. The customized sealing member according to claim 1, wherein the surface geometry data has first data representing a localized region of the surface geometry; and wherein the providing step further comprises:
   employing the first data to generate second data representing each respective set of first coordinates and third data representing each respective set of second coordinates.

8. The customized sealing member according to claim 7, wherein each respective set of first coordinates and each respective set of second coordinates is a corresponding set of three-dimensional coordinates; and wherein each of the first plurality of rollers and the second plurality of rollers comprises a respective body portion and a respective shelf portion extending outwardly from the respective body portion.

9. The customized sealing member according to claim 7, wherein the employing step comprises:
   generating the second data and the third data such that each respective set of first three-dimensional coordinates and each respective set of second three-dimensional coordinates is spaced a corresponding predetermined distance in a corresponding predetermined direction from the localized region.

10. The customized sealing member according to claim 1, wherein the process further comprises the step of:
    coupling the coupling portion to the end portion after the end portion moves around the inner directing portion.

11. The customized sealing member according to claim 1, wherein, when the stock of material is inserted between the inner directing portion and the outer directing portion, the stock of material maintains a uniform cross-sectional profile.

12. The customized sealing member according to claim 1, wherein the stock of material has an elongated planar portion and an elongated cylindrical-shaped portion extending from the planar portion; wherein the planar portion is structured to be coupled to the support member; wherein the cylindrical-shaped portion has a thru hole extending longitudinally therethrough; and wherein the cylindrical-shaped portion is structured to engage and provide a seal with the face of the patient.

13. The customized sealing member according to claim 12, wherein the stock of material has a plurality of edge portions each defining a perforation;
    and wherein each respective one of the perforations is in fluid communication with the thru hole.

14. A customized mask comprising:
    the customized sealing member according to claim 1; and
    a support member coupled to the customized sealing member.

15. The customized mask according to claim 14, wherein the customized sealing member has a planar portion and a cylindrical-shaped portion extending from the planar portion; wherein the planar portion is coupled to the support member; and wherein the cylindrical-shaped portion is structured to engage and provide a seal with the face of the patient.

16. The customized mask according to claim 14, wherein the customized sealing member has a plurality of perforations; wherein the support member comprises a nose bridge region and a chin region disposed opposite the nose bridge region; wherein the nose bridge region comprises a first retaining portion, a second retaining portion and a first shelf portion extending between the first and second retaining portions; wherein the first and second retaining portions and the first shelf portion each engage the customized sealing member; wherein the first shelf portion has a recessed channel portion; wherein the chin region comprises a third retaining portion, a second shelf portion extending from the third retaining portion, and a third shelf portion spaced from the second shelf portion; wherein each of the third retaining portion and the second shelf portion engages the customized sealing member; and wherein the third shelf portion is spaced from the customized sealing member in order to provide a fluid pathway from an interior of the customized mask through the recessed channel portion to each of the perforations.

17. A method of manufacturing a customized sealing member for a customized mask, the customized mask comprising a support member, the method comprising the steps of:
    generating surface geometry data of a face of a patient, the surface geometry data corresponding to and representing a surface geometry of the face of the patient;
    providing a directing apparatus shaped according to the surface geometry data, the directing apparatus comprising an inner directing portion defining a first closed curve shaped according to the surface geometry data, and an outer directing portion defining a second closed curve shaped according to the surface geometry data, the directing apparatus being structured to receive and direct a stock of material, the stock of material comprising an end portion and a coupling portion disposed opposite the end portion, wherein the inner directing portion comprises a first plurality of rollers each having a set of first coordinates, and wherein the outer directing portion comprises a second plurality of rollers each having a set of second coordinates;
    inserting the stock of material into the directing apparatus in order to produce the customized sealing member;
    inserting the stock of material between the inner directing portion and the outer directing portion; and
    moving the end portion around the first closed curve defined by the inner directing portion such that as the end portion moves around the inner directing portion, the coupling portion moves toward the inner directing portion until the coupling portion and the end portion meet when the end portion has moved around the first closed curve defined by the inner directing portion.

* * * * *